United States Patent
Scholl et al.

(10) Patent No.: US 11,213,326 B2
(45) Date of Patent: *Jan. 4, 2022

(54) SYSTEMS AND METHODS FOR PERFORMING SPINE SURGERY

(71) Applicant: NuVasive, Inc., San Diego, CA (US)

(72) Inventors: Thomas Scholl, San Diego, CA (US); D J Geiger, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 16/655,172

(22) Filed: Oct. 16, 2019

(65) Prior Publication Data

US 2020/0046409 A1 Feb. 13, 2020

Related U.S. Application Data

(63) Continuation of application No. 15/879,397, filed on Jan. 24, 2018, now Pat. No. 10,485,589, which is a
(Continued)

(51) Int. Cl.
*A61B 17/70* (2006.01)
*A61B 17/88* (2006.01)
(Continued)

(52) U.S. Cl.
CPC ...... *A61B 17/7083* (2013.01); *A61B 17/8863* (2013.01); *A61B 90/06* (2016.02);
(Continued)

(58) Field of Classification Search
CPC ........... A61B 17/7083; A61B 17/8863; A61B 17/087; A61B 17/025; A61B 17/3421; A61B 17/7005; A61B 17/7014; A61B 17/7017; A61B 17/7023; A61B 17/7028; A61B 17/7037; A61B 17/7038; A61B 17/7044; A61B 17/708; A61B 17/7082;
(Continued)

(56) References Cited

U.S. PATENT DOCUMENTS 3,365,804 A 1/1968 Fjellstrom
4,282,737 A 8/1981 Maples
(Continued)

FOREIGN PATENT DOCUMENTS

CN 202982181 U 6/2013
DE 10314882 A1 10/2004
(Continued)

OTHER PUBLICATIONS

Ames, C et al., "Impact of Spinopelvic Alignment on Decision Making in Deformity Surgery in Adults: A Review," J Neurosurg Spine 16: 547-564, 2012.
(Continued)

*Primary Examiner* — Pedro Philogene

(57) ABSTRACT

A digitizer pointer is provided as part of a system for correcting a curvature or deformity in a patient's spine based on the digitized locations of implanted screws and tracking the placement of the rod as it is placed in a minimally invasive fashion. The digitizer pointer is includes an offset adjustment feature, a swivel feature, and a translation feature.

20 Claims, 3 Drawing Sheets

Related U.S. Application Data continuation of application No. 14/887,246, filed on Oct. 19, 2015, now Pat. No. 9,913,669.

(60) Provisional application No. 62/065,531, filed on Oct. 17, 2014.

(51) Int. Cl.

| | | |
|---|---|---|
| *A61B 90/00* | (2016.01) | |
| *A61B 17/00* | (2006.01) | |
| *B21D 7/02* | (2006.01) | |
| *B21D 7/024* | (2006.01) | |
| *B21D 7/04* | (2006.01) | |
| *B21D 7/06* | (2006.01) | |

(52) U.S. Cl.
CPC .... *A61B 90/39* (2016.02); *A61B 2017/00221* (2013.01); *A61B 2090/3987* (2016.02); *A61B 2090/3991* (2016.02); *B21D 7/021* (2013.01); *B21D 7/024* (2013.01); *B21D 7/04* (2013.01); *B21D 7/063* (2013.01)

(58) Field of Classification Search
CPC ............ A61B 17/7085; A61B 17/7091; A61B 17/7004; A61B 17/701; A61B 17/7032; A61B 17/704; A61B 17/8897; A61B 17/1655; A61B 90/06; A61B 90/39; A61B 2090/3987; A61B 2090/3991; A61B 2090/061; A61B 2017/00261; A61B 2017/0256; A61B 2017/00221; B21D 7/021; B21D 7/024; B21D 7/04; B21D 7/063

See application file for complete search history.

(56) References Cited

U.S. PATENT DOCUMENTS

| | | | |
|---|---|---|---|
| 4,474,046 A | 10/1984 | Cook | |
| 4,773,402 A | 9/1988 | Asher | |
| 5,113,685 A | 5/1992 | Asher | |
| 5,161,404 A | 11/1992 | Hayes | |
| 5,257,184 A | 10/1993 | Mushabac | |
| 5,290,289 A | 3/1994 | Sanders | |
| 5,365,996 A | 11/1994 | Crook | |
| 5,389,099 A | 2/1995 | Hartmeister | |
| 5,490,409 A | 2/1996 | Weber | |
| 5,548,985 A | 8/1996 | Yapp | |
| 5,658,286 A | 8/1997 | Sava | |
| 5,672,175 A | 9/1997 | Martin | |
| 5,682,886 A | 11/1997 | Delp | |
| 5,704,937 A | 1/1998 | Martin | |
| 5,768,134 A | 6/1998 | Swaelens | |
| 5,806,521 A | 9/1998 | Morimoto | |
| 5,819,571 A | 10/1998 | Johnson | |
| 5,819,580 A | 10/1998 | Gauthier | |
| 5,901,600 A | 5/1999 | Decker | |
| 6,006,581 A | 12/1999 | Holmes | |
| 6,035,691 A | 3/2000 | Lin | |
| 6,205,411 B1 | 3/2001 | Digioia, III | |
| 6,226,548 B1 | 5/2001 | Foley | |
| 6,236,875 B1 | 5/2001 | Bucholz | |
| 6,301,495 B1 | 10/2001 | Gueziec | |
| 6,327,491 B1 | 12/2001 | Franklin | |
| 6,332,780 B1 | 12/2001 | Traxel | |
| 6,347,240 B1 | 2/2002 | Foley | |
| 6,529,765 B1 | 3/2003 | Franck | |
| 6,578,280 B2 | 6/2003 | Kinoshita | |
| 6,644,087 B1 | 11/2003 | Ralph | |
| 6,701,174 B1 | 3/2004 | Krause | |
| 6,906,724 B2 | 6/2005 | Lake | |
| 6,978,188 B1 | 12/2005 | Christensen | |
| 7,206,626 B2 | 4/2007 | Quaid, III | |
| 7,454,939 B2 | 11/2008 | Garner | |
| 7,837,467 B2 | 11/2010 | Butscher | |
| 9,526,537 B2 * | 12/2016 | Meyer | A61B 17/7086 |
| 9,913,669 B1 * | 3/2018 | Scholl | A61B 17/8863 |
| 10,485,589 B2 * | 11/2019 | Scholl | A61B 17/8863 |
| 2002/0007294 A1 | 1/2002 | Bradbury | |
| 2002/0133097 A1 | 9/2002 | Leitner | |
| 2002/0183610 A1 | 12/2002 | Foley | |
| 2003/0055435 A1 | 3/2003 | Barrick | |
| 2003/0055502 A1 | 3/2003 | Lang | |
| 2003/0149351 A1 | 8/2003 | Nowinski | |
| 2003/0205075 A1 | 11/2003 | Strippgen | |
| 2003/0215122 A1 | 11/2003 | Tanaka | |
| 2004/0068187 A1 | 4/2004 | Krause | |
| 2004/0097952 A1 | 5/2004 | Sarin | |
| 2004/0122549 A1 | 6/2004 | Otsuki | |
| 2004/0133276 A1 | 7/2004 | Lang | |
| 2004/0147927 A1 | 7/2004 | Tsougarakis | |
| 2004/0152972 A1 | 8/2004 | Hunter | |
| 2004/0158260 A1 | 8/2004 | Blau | |
| 2004/0167637 A1 | 8/2004 | Biscup | |
| 2005/0054917 A1 | 3/2005 | Kitson | |
| 2005/0074304 A1 * | 4/2005 | Couture | A61B 90/36 408/110 |
| 2005/0101966 A1 | 5/2005 | Lavallee | |
| 2005/0119593 A1 | 6/2005 | Gallard | |
| 2005/0149050 A1 | 7/2005 | Stifter | |
| 2005/0182320 A1 | 8/2005 | Stifter | |
| 2005/0192575 A1 | 9/2005 | Pacheco | |
| 2005/0203511 A1 | 9/2005 | Wilson-MacDonald | |
| 2005/0245817 A1 | 11/2005 | Clayton | |
| 2005/0251139 A1 | 11/2005 | Roh | |
| 2005/0262911 A1 | 12/2005 | Dankowicz | |
| 2005/0288809 A1 | 12/2005 | Spaeth | |
| 2006/0005601 A1 | 1/2006 | Widmayer | |
| 2006/0015030 A1 | 1/2006 | Poulin | |
| 2006/0094951 A1 | 5/2006 | Dean | |
| 2006/0120583 A1 | 6/2006 | Dewaele | |
| 2006/0150699 A1 | 7/2006 | Garner | |
| 2006/0212158 A1 | 9/2006 | Miller | |
| 2006/0235338 A1 | 10/2006 | Pacheco | |
| 2006/0247864 A1 | 11/2006 | Tamez-Pena | |
| 2006/0264934 A1 | 11/2006 | Fallin | |
| 2006/0264973 A1 | 11/2006 | Abdelgany | |
| 2006/0282020 A1 | 12/2006 | Bertagnoli | |
| 2007/0066917 A1 | 3/2007 | Hodorek | |
| 2007/0093824 A1 | 4/2007 | Hestad | |
| 2007/0093998 A1 | 4/2007 | El-Baroudi | |
| 2007/0118055 A1 | 5/2007 | McCombs | |
| 2007/0118243 A1 | 5/2007 | Schroeder | |
| 2007/0142751 A1 | 6/2007 | Kang | |
| 2007/0198022 A1 | 8/2007 | Lang | |
| 2007/0227216 A1 | 10/2007 | Schalliol | |
| 2007/0233246 A1 | 10/2007 | Trieu | |
| 2007/0239159 A1 | 10/2007 | Altarac | |
| 2007/0250169 A1 | 10/2007 | Lang | |
| 2007/0276501 A1 | 11/2007 | Betz | |
| 2008/0009945 A1 | 1/2008 | Pacheco | |
| 2008/0039717 A1 | 2/2008 | Frigg | |
| 2008/0065067 A1 | 3/2008 | Steinberg | |
| 2008/0154120 A1 | 6/2008 | Von Jako | |
| 2008/0167547 A1 | 7/2008 | Bova | |
| 2008/0208080 A1 | 8/2008 | Ichikawa | |
| 2008/0269596 A1 | 10/2008 | Revie | |
| 2008/0269898 A1 | 10/2008 | Carls | |
| 2008/0269906 A1 | 10/2008 | Iannotti | |
| 2008/0288229 A1 | 11/2008 | Arvizo | |
| 2008/0306490 A1 | 12/2008 | Lakin | |
| 2009/0022382 A1 | 1/2009 | Feikas | |
| 2009/0024164 A1 | 1/2009 | Neubardt | |
| 2009/0043556 A1 | 2/2009 | Axelson | |
| 2009/0082666 A1 | 3/2009 | Geist | |
| 2009/0089034 A1 | 4/2009 | Penney | |
| 2009/0093852 A1 | 4/2009 | Hynes | |
| 2009/0099605 A1 | 4/2009 | Fallin | |
| 2009/0132050 A1 | 5/2009 | Holm | |
| 2009/0149977 A1 | 6/2009 | Schendel | |
| 2009/0157083 A1 | 6/2009 | Park | |
| 2009/0157185 A1 | 6/2009 | Kim | |
| 2009/0209851 A1 | 8/2009 | Blau | |

(56) References Cited

U.S. PATENT DOCUMENTS

| | | |
|---|---|---|
| 2009/0209884 A1 | 8/2009 | Van Vorhis |
| 2009/0226055 A1 | 9/2009 | Dankowicz |
| 2009/0226068 A1 | 9/2009 | Fitz |
| 2009/0249851 A1 | 10/2009 | Isaacs |
| 2009/0254097 A1 | 10/2009 | Isaacs |
| 2009/0276045 A1 | 11/2009 | Lang |
| 2010/0030231 A1 | 2/2010 | Revie |
| 2010/0030232 A1 | 2/2010 | Zehavi |
| 2010/0076563 A1 | 3/2010 | Otto |
| 2010/0100011 A1 | 4/2010 | Roche |
| 2010/0101295 A1 | 4/2010 | Miller |
| 2010/0111631 A1 | 5/2010 | Trieu |
| 2010/0145663 A1 | 6/2010 | Skalli |
| 2010/0177946 A1 | 7/2010 | De Bruijne |
| 2010/0191071 A1 | 7/2010 | Anderson |
| 2010/0191088 A1 | 7/2010 | Anderson |
| 2010/0191100 A1 | 7/2010 | Anderson |
| 2010/0234725 A1 | 9/2010 | Geist |
| 2010/0292795 A1 | 11/2010 | Jensen |
| 2010/0292963 A1 | 11/2010 | Schroeder |
| 2010/0329530 A1 | 12/2010 | Lang |
| 2010/0332197 A1 | 12/2010 | Melton |
| 2010/0332248 A1 | 12/2010 | Pettersson |
| 2011/0010187 A1 | 1/2011 | Andersson |
| 2011/0015514 A1 | 1/2011 | Skalli |
| 2011/0040340 A1 | 2/2011 | Miller |
| 2011/0066193 A1 | 3/2011 | Lang |
| 2011/0071802 A1 | 3/2011 | Bojarski |
| 2011/0093023 A1 | 4/2011 | Lee |
| 2011/0093108 A1 | 4/2011 | Ashby |
| 2011/0094278 A1 | 4/2011 | Caporusso |
| 2011/0107270 A1 | 5/2011 | Wang |
| 2011/0144752 A1 | 6/2011 | Defelice |
| 2011/0196426 A1 | 8/2011 | Peukert |
| 2011/0245871 A1 | 10/2011 | Williams |
| 2011/0257653 A1 | 10/2011 | Hughes |
| 2011/0265538 A1 | 11/2011 | Trieu |
| 2011/0266265 A1 | 11/2011 | Lang |
| 2011/0268325 A1 | 11/2011 | Teichman |
| 2011/0270262 A1 | 11/2011 | Justis |
| 2011/0295378 A1 | 12/2011 | Bojarski |
| 2011/0305379 A1 | 12/2011 | Mahfouz |
| 2011/0307020 A1 | 12/2011 | Geist |
| 2011/0319745 A1 | 12/2011 | Frey |
| 2012/0010710 A1 | 1/2012 | Frigg |
| 2012/0016423 A1 | 1/2012 | Hua |
| 2012/0047980 A1 | 3/2012 | Harper |
| 2012/0063655 A1 | 3/2012 | Dean |
| 2012/0116203 A1 | 5/2012 | Vancraen |
| 2012/0141034 A1 | 6/2012 | Iannotti |
| 2012/0178069 A1 | 7/2012 | McKenzie |
| 2012/0186411 A1 | 7/2012 | Lodahi |
| 2012/0191192 A1 | 7/2012 | Park |
| 2012/0209394 A1 | 8/2012 | Bojarski |
| 2012/0230566 A1 | 9/2012 | Dean |
| 2012/0247173 A1 | 10/2012 | Paris |
| 2012/0274631 A1 | 11/2012 | Friedland |
| 2012/0290272 A1 | 11/2012 | Bryan |
| 2012/0310364 A1 | 12/2012 | Li |
| 2012/0323279 A1 | 12/2012 | Tsuang |
| 2012/0325363 A1 | 12/2012 | Knebl |
| 2013/0053854 A1 | 2/2013 | Schoenefeld |
| 2013/0072982 A1* | 3/2013 | Simonson ......... A61B 17/7083 606/267 |
| 2013/0073315 A1 | 3/2013 | Cardamone |
| 2013/0090692 A1 | 4/2013 | Nuckley |
| 2013/0091921 A1 | 4/2013 | Wilcox |
| 2013/0110174 A1 | 5/2013 | Marik |
| 2013/0123850 A1 | 5/2013 | Schoenefeld |
| 2013/0131486 A1 | 5/2013 | Copf |
| 2013/0166256 A1 | 6/2013 | Wirx-Speetjens |
| 2013/0211531 A1 | 8/2013 | Steines |
| 2013/0218163 A1 | 8/2013 | Frey |
| 2013/0238096 A1 | 9/2013 | Kotlus |
| 2013/0245803 A1 | 9/2013 | Lang |
| 2013/0268007 A1 | 10/2013 | Rezach |
| 2013/0296954 A1 | 11/2013 | Skaggs |
| 2013/0304217 A1 | 11/2013 | Recber |
| 2013/0307955 A1 | 11/2013 | Deitz |
| 2013/0325069 A1 | 12/2013 | Pereiro De Lamo |
| 2013/0332128 A1 | 12/2013 | Miles |
| 2013/0345757 A1 | 12/2013 | Stad |
| 2014/0025181 A1 | 1/2014 | Vanasse |
| 2014/0066994 A1 | 3/2014 | Dominik |
| 2014/0074438 A1 | 3/2014 | Furrer |
| 2014/0076883 A1 | 3/2014 | Brailovski |
| 2014/0081400 A1 | 3/2014 | Azernikov |
| 2014/0137618 A1 | 5/2014 | Isaacs |
| 2014/0213889 A1 | 7/2014 | Macht |
| 2014/0244220 A1 | 8/2014 | McKinnon |
| 2014/0257508 A1 | 9/2014 | Bojarski |
| 2014/0311203 A1 | 10/2014 | Crawford |
| 2014/0364916 A1 | 12/2014 | Lorio |

FOREIGN PATENT DOCUMENTS

| | | |
|---|---|---|
| DE | 102004008870 A1 | 10/2004 |
| EP | 1413257 A1 | 10/2002 |
| EP | 1426023 A1 | 10/2003 |
| EP | 1657681 A1 | 5/2006 |
| EP | 2017785 A1 | 1/2009 |
| EP | 2522295 A1 | 11/2012 |
| JP | 2013230221 A | 11/2013 |
| WO | WO-2003030787 A1 | 4/2003 |
| WO | WO-2004070581 A2 | 8/2004 |
| WO | WO-2006055998 A1 | 6/2006 |
| WO | WO-2007009263 A1 | 1/2007 |
| WO | WO-2008021494 A2 | 2/2008 |
| WO | WO-2008101090 A2 | 8/2008 |
| WO | WO-2008130355 A1 | 10/2008 |
| WO | WO-2009035358 A1 | 3/2009 |
| WO | WO-2009140294 A1 | 11/2009 |
| WO | WO-2010099231 A2 | 9/2010 |
| WO | WO-2012061452 A1 | 5/2012 |
| WO | WO-2012062464 A1 | 5/2012 |
| WO | WO-2012135653 A1 | 10/2012 |
| WO | WO-2012152900 A1 | 11/2012 |
| WO | WO-2013087082 A1 | 6/2013 |
| WO | WO-2013134623 A1 | 9/2013 |
| WO | WO-2013150233 A1 | 10/2013 |
| WO | WO-2014016824 A1 | 1/2014 |
| WO | WO-2013041618 A1 | 3/2014 |
| WO | WO-2014037093 A1 | 3/2014 |
| WO | WO-2014048448 A1 | 4/2014 |
| WO | WO-2014070889 A1 | 5/2014 |
| WO | WO-2014079812 A1 | 5/2014 |
| WO | WO-2014088801 A1 | 6/2014 |
| WO | WO-2014107144 A1 | 7/2014 |

OTHER PUBLICATIONS

Aubin, C et al., "Preoperative Planning Simulator for Spinal Deformity Surgeries," Spine vol. 33, No. 20, pp. 2143-2152, 2008.

Langlotz et al. "A Pilot Study on Computer-Assisted Optimal Contouring of Orthopedic Fixation Devices". Computer Aided Surgery vol. 4 (1999): 305-313.

Le Huec, J et al., "Equilibrium of the Human Body and the Gravity Line: The Basics," Eur Spine J (2011) 20 (Suppl 5):S558-S563.

Roussouly, P et al., "Sagittal Parameters of the Spine: Biomechanical Approach," Eur Spine J (2011) 20 (Suppl 5):S578-S585.

Schwab, F et al., "Adult Spinal Deformity—Postoperative Standing Imbalance, How Much Can You Tolerate? An Overview of Key Parameters in Assessing Alignment and Planning Corrective Surgery," Spine vol. 35, No. 25, 2224-2231, 2010.

Terran, J et al., "The SRS-Schwab Adult Spinal Deformity Classification: Assessment and Clinical Correlations Based on a Perspective Operative and Nonoperative Cohort," Neurosurgery 73: 559-568, 2013.

Goodrich and Volcan, eds., "Spinal Alignment and Correction in Adults," eXtreme Lateral Interbody Fusion (XLIF®), $2^{nd}$ Edition,

(56) References Cited

OTHER PUBLICATIONS

2013, Chapter 9, 91-115, Quality Medical Publishing, Inc., St. Louis, Missouri.

* cited by examiner

SYSTEMS AND METHODS FOR PERFORMING SPINE SURGERY

CROSS-REFERENCE TO RELATED APPLICATIONS

This application claims priority to and is a continuation of U.S. patent application Ser. No. 15/879,397, filed Jan. 24, 2018 (currently pending), which claims priority to and is a continuation of U.S. patent application Ser. No. 14/887,246, filed Oct. 19, 2015, and issued on Mar. 13, 2018 as U.S. Pat. No. 9,913,669, which claims priority to U.S. Provisional Application Ser. No. 62/065,531, filed on Oct. 17, 2014 and entitled "Systems and Methods of Performing Spine Surgery," the complete disclosure of which is hereby incorporated by reference into this application as if set forth fully herein.

FIELD

The present application pertains to spine surgery. More particularly, the present application pertains to systems and methods related to the planning, design, formation, and implantation of spinal implants.

BACKGROUND

The spinal column is a highly complex system of bones and connective tissues that provide support for the body and protect the delicate spinal cord and nerves. The spinal column includes a series of vertebral bodies stacked atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the endplates of the upper and lower vertebrae are inclined towards one another.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, degenerative disc disease, fractured vertebrae, and the like). Patients that suffer from such conditions often experience extreme and debilitating pain, as well as diminished nerve function. Posterior fixation for spinal fusions, decompression, deformity, and other reconstructions are performed to treat these patients. The aim of posterior fixation in lumbar, thoracic, and cervical procedures is to stabilize the spinal segments, correct multi-axis alignment, and aid in optimizing the long-term health of the spinal cord and nerves.

Screws, hooks, and rods are devices used to stabilize the spine during a spinal fixation procedure. Such procedures often require the instrumentation of many bony elements. The devices, for example rods, can be extremely challenging to design and implant into the patient. Spinal rods are usually formed of stainless steel, titanium, cobalt chrome, or other similarly hard metal, and as such are difficult to bend without some sort of leverage-based bender. Moreover, a spinal rod needs to be oriented in six degrees of freedom to compensate for the anatomical structure of a patient's spine as well as the attachment points (screws, hooks) for securing the rod to the vertebrae. Additionally, the physiological problem being treated as well as the physician's preferences will determine the exact configuration necessary. Accordingly, the size, length, and particular bends of the spinal rod depends on the size, number, and position of each vertebrae to be constrained, the spatial relationship amongst vertebrae, as well as the screws and hooks used to hold the rods attached to the vertebrae.

The bending of a spinal rod can be accomplished by a number of methods. The most widely used method is a three-point bender called a French Bender. The French bender is a pliers-like device that is manually operated to place one or more bends in a rod. The French bender requires both handles to operate and provides leverage based on the length of the handle. The use of the French bender requires a high degree of physician skill because the determination of the location, angle, and rotation of bends is often subjective and can be difficult to correlate to a patient's anatomy. Other methods of bending a rod to fit a screw and/or hook construct include the use of an in-situ rod bender and a keyhole bender. However, all of these methods can be subjective, iterative, and are often referred to as an "art." As such, rod bending and reduction activities can be a time consuming and potentially frustrating step in the finalization of a complex and/or long spinal construct. Increased time in the operating room to achieve optimum bending can be costly to the patient and increase the chance of the morbidity. When rod bending is performed poorly, the rod can preload the construct and increase the chance of failure of the fixation system. The bending and re-bending involved can also promote metal fatigue and the creation of stress risers in the rod.

Efforts directed to computer-aided design or shaping of spinal rods have been largely unsuccessful due to the lack of bending devices as well as lack of understanding of all of the issues involved in bending surgical devices. U.S. Pat. No. 7,957,831, issued Jun. 7, 2011 to Isaacs, describes a rod bending system which includes a spatial measurement subsystem with a digitizer to obtain the three dimensional location of surgical implants (screws, hooks), software to convert the implant locations to a series of bend instructions, and a mechanical rod bender used to execute the bend instructions such that the rod will be bent precisely to custom fit within each of the screws. This is advantageous because it provides quantifiable rod bending steps that are customized to each patient's anatomy enabling surgeons to create custom-fit rods on the first pass, thereby increasing the speed and efficiency of rod bending, particularly in complex cases. This, in turn, reduces the morbidity and cost associated with such procedures. However, a need still exists for improved rod bending systems that allow for curvature and deformity correction in fixation procedures, provide the user with more rod bending options, and accommodate more of the user's clinical preferences including the ability to determine the spatial orientation of the tip of the rod and the tip of the rod pusher relative to one another.

SUMMARY

The present disclosure describes a digitizer pointer configured for use as part of a surgical rod bending system. More specifically, digitizer pointer comprises a part of a spatial tracking system used to obtain the location of one or more surgical implants during a surgical procedure. The digitizer pointer includes an adjustable offset feature to allow the user to digitize a point above the actual implant, a swivel feature that allows the distal end of the and the proximal end to swivel relative to one another and a translation feature that allows the distal end to mate with any number of instrumentation types in any number of surgical procedures.

By way of example, the digitizer pointer includes a proximal portion, a middle portion, and a distal portion. The proximal portion, middle portion, and distal portion comprise separate pieces that are assembled to form a single generally cylindrical elongated instrument. The proximal portion includes an elongate tubular member and an inner piston. The inner piston includes a threaded post at the proximal end for mating with additional tracking instrumentation, for example an IR-reflective tracking array. The elongate tubular member and inner piston comprise the adjustable offset feature component of the digitizer pointer.

The swivel feature includes several elements positioned on the distal end of the elongated tubular member working in concert with several elements positioned on the proximal end of the middle portion. The distal end of the elongate tubular member comprises a smooth cylindrical post. A circumferential recess is formed within the cylindrical post, and a raised lip is positioned at the proximal end of the cylindrical post. The proximal end of the middle portion comprises a swivel housing including a cylindrical cavity sized and configured to receive the cylindrical post therein. Retention pins extend through pin apertures in the swivel housing and into the cavity. Upon assembly, the retention pins occupy space in the circumferential recess, and allow for rotational (swivel) movement of the cylindrical post while ensuring the cylindrical post remains within the cavity. The raised lip interfaces with the rim of the cavity to form a swivel interface.

By way of example, the swivel feature may be desirable, according to surgeon preference to re-orient a screw-tulip to align with the other screws (and eventual rod) within a construct. For example, after the digitizer pointer is engaged with a spinal implant (e.g bone screw), the user may manually hold the distal portion of the digitizer pointer (e.g. any suitable place distal of the swivel interface) and swivel the proximal portion of the digitizer pointer (e.g. any suitable place proximal of the swivel interface) about the swivel feature. The proximal portion of the digital pointer is then rotated until the IR array (attached to the threaded post) comes in view of the camera.

The translation feature includes several elements positioned on the middle portion working in concert with several elements positioned on the distal portion. In addition to the swivel housing, the middle portion includes an elongate shaft extending distally from the swivel housing. The elongate shaft includes a proximal segment and a distal segment. By way of example, the proximal segment may have a different width dimension (e.g. diameter) than the distal segment. In the example shown and described herein, the proximal segment has a width diameter that is greater than the width dimension of the distal segment. The proximal segment has a smooth surface to facilitate translation of the distal portion. The proximal segment further has a guide pin extending laterally away from the smooth surface positioned approximately in the middle of the proximal segment. The guide pin is received within the shaped track to help control translation of the distal portion, as will be explained. The distal segment extends distally from the proximal segment and includes a hex lobe attachment feature positioned at the distal end. The hex lobe attachment feature is configured to engage a spinal implant, for example a bone screw head. A spring is positioned about the proximal segment and is configured to exert a force on the distal portion to bias the distal portion in an extended position (in which the hex lobe attachment feature is positioned within the fork member.

The distal portion comprises an outer sleeve having a track housing at the proximal end, a fork member at the distal end, and an interior lumen extending through the entire length of the distal portion. The interior lumen is sized and configured to slideably receive the distal segment of the middle portion therein. The track housing includes a shaped track configured to receive the pin therein. The track has a first lock slot positioned at the proximal end of the shaped track and a second lock slot positioned at the distal end of the shaped track. The fork member includes a pair of parallel extensions having shaped ends configured to engage a portion of a spinal implant, for example a tulip portion of a rod-receiving bone screw.

The spring exerts a force on the distal portion that biases the distal portion in an extended position. In this position, the guide pin is positioned within the first lock slot at the proximal end of the shaped track. A user may manually engage (e.g. grab) the track housing and rotate the housing such that the guide pin is urged out of the first lock slot, along the main portion of the shaped track, and into the second lock slot. As this happens, the distal portion will be experience translation in a proximal direction. When the guide pin is fully resting in the second lock slot after translation, the hex lobe attachment feature of the middle portion will extend beyond the fork member.

The translating feature allows the surgeon to perform two digitizing methods depending on the surgical procedure and the goals of the surgical procedure. In the first setting (in which the guide pin is in the first lock slot), the hex lobe attachment feature is in a retracted position (since the distal portion is extended), and the digitizer pointer can digitize all open, fixed, and connector tulips via engagement between the implanted device and the fork member. In the second setting (in which the pin is in the second lock slot), the hex lobe attachment feature extends past the distal ends of the fork member, and the digitizer pointer can digitize when there has been a lock screw placed. The hex lobe attachment feature mates with a lock screw and allows the surgeon to digitize the location of the temporary rod placement. Thus, the surgeon can digitize where the spine is during the temporary rod placement and when final rod bending is being achieved, for example during a pedicle subtraction osteotomy procedure.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
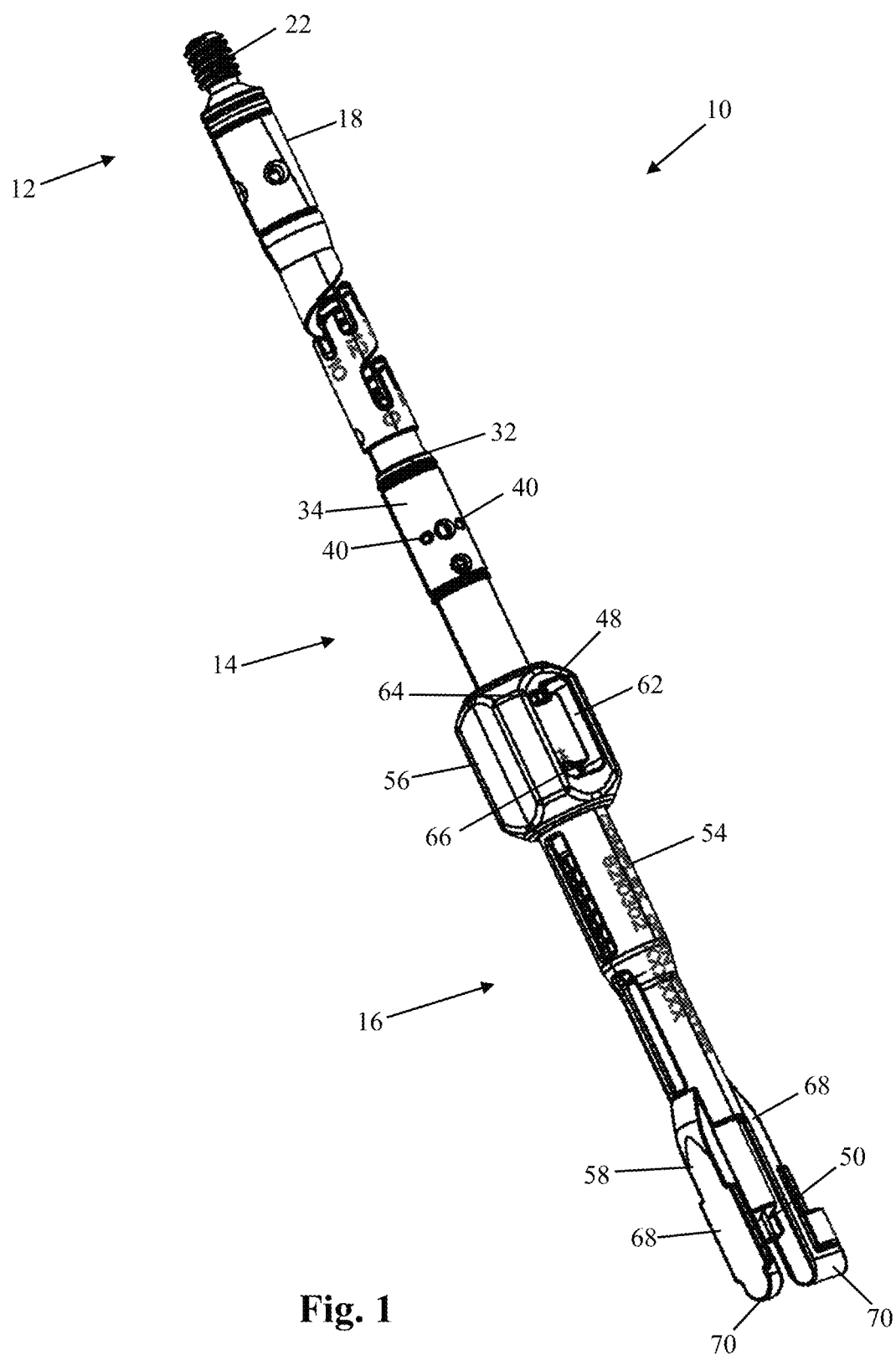
FIG. 1 is a perspective view of an example of a digitizer pointer according to one embodiment.

Illustrative embodiments of the invention are described below. In the interest of clarity, not all features of an actual implementation are described in this specification. It will of course be appreciated that in development of any such actual embodiment, numerous implantation-specific decisions must be made to achieve the developers' specific goals such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

The digitizer pointer 10 of the present disclosure is configured to be used as part of a surgical rod bending system, for example the surgical rod bending systems shown and described in commonly-owned U.S. Pat. No. 8,539,888, issued Oct. 8, 2013 and entitled "System and Device for Designing and Forming a Surgical Implant," and commonly-owned and co-pending U.S. patent application Ser. No. 13/815,643, filed Mar. 12, 2013 and entitled "System and Method for Performing Spinal Surgery," the entire contents of each of which are hereby incorporated by reference into this disclosure as if set forth fully herein. More specifically, digitizer pointer comprises a part of a spatial tracking system used to obtain the location of one or more surgical implants during a surgical procedure. In addition to the spatial tracking system, the surgical bending systems described in the '888 patent and '643 application also include a control unit containing software to convert the implant locations to a series of bend instructions, and a mechanical rod bender to receive the bend instructions and effect precise bends in the rod. In addition to the adjustable offset feature previously disclosed (and incorporated by reference into this disclosure), the digitizer pointer 10 of the present disclosure includes a swivel feature that allows the distal end and the proximal end to swivel relative to one another and a translation feature that allows the distal end to mate with any number of instrumentation types in any number of surgical procedures.

Generally, the spatial tracking system includes an IR sensor, a digitizer pointer, as well as other components including Host USB converter. The spatial tracking system is in communication with control unit. The control unit has spatial relation software and is communicatively linked to the display so that information relevant to the surgical procedure may be conveyed to the user in a meaningful manner. By way of example, the relevant information includes, but is not limited to, spatial positioning data acquired by the IR sensor (e.g., translational data in the x, y, and z axes and orientation/rotational data $R_x$, $R_y$, and $R_z$). A neuromonitoring system may be communicatively linked to the spatial tracking system via the control unit. By way of example only, the neuromonitoring system may be the neuromonitoring system shown and described in U.S. Pat. No. 8,255,045, entitled "Neurophysiologic Monitoring System" and filed on Apr. 3, 2008, the entire contents of which are hereby incorporated by reference as if set forth fully herein. Once the user has digitized the implant locations and selected the desired rod solution, the user then executes the bends using a mechanical rod bender.

Figure 2:
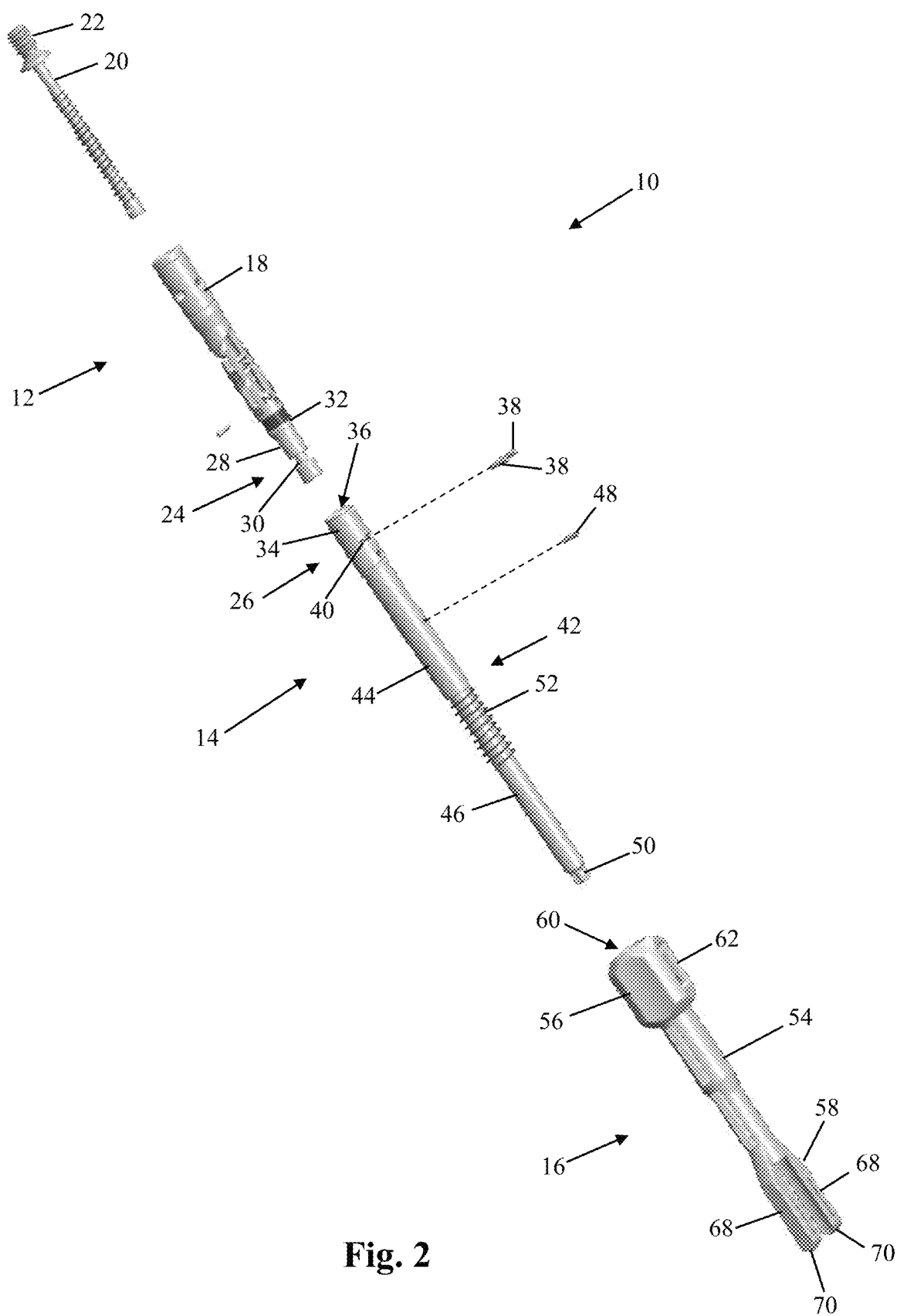
FIG. 2 is an exploded perspective view of the digitizer pointer of FIG. 1.
Figure 3:
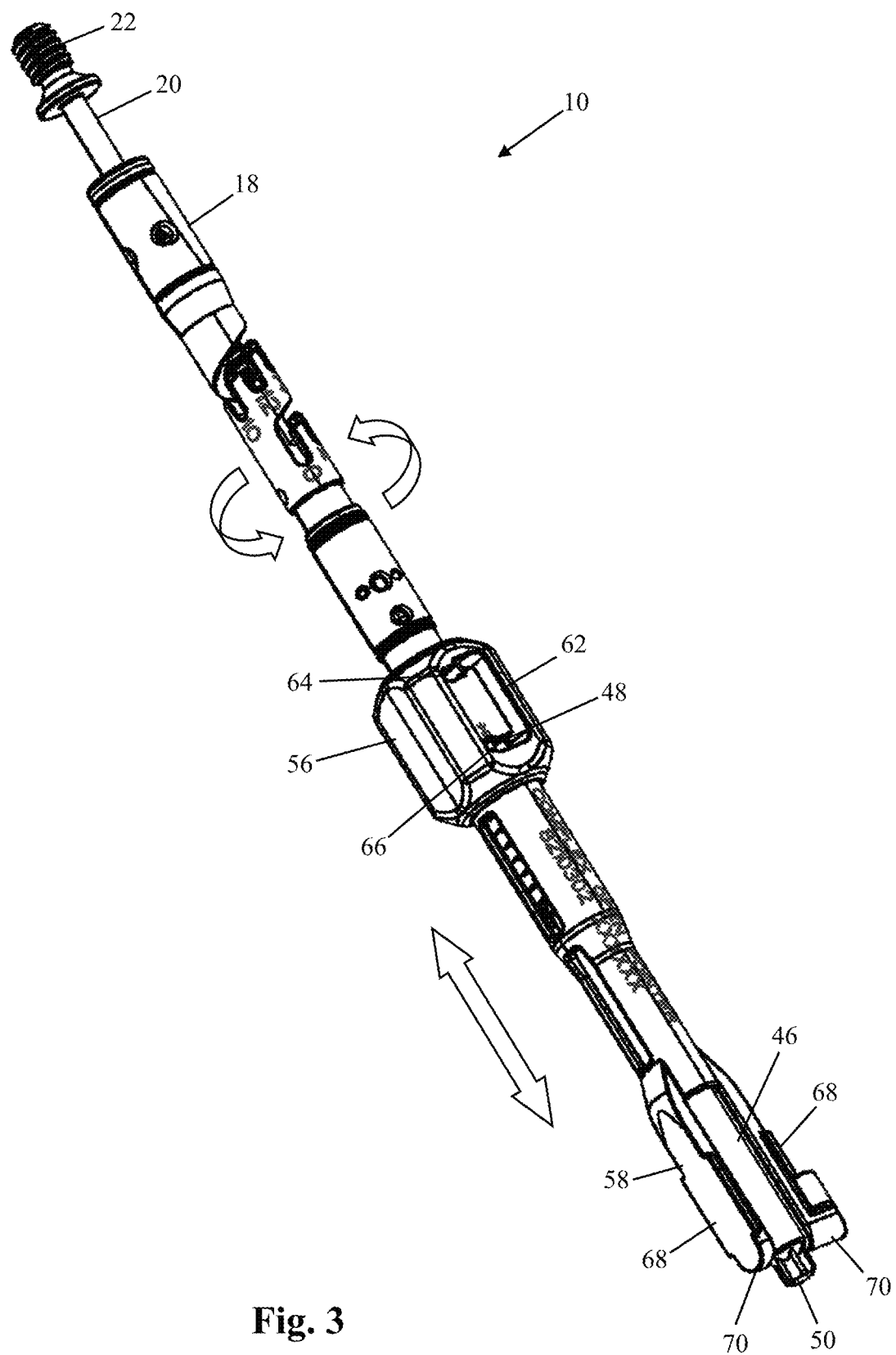
FIG. 3 is a perspective view of the digitizer pointer of FIG. 1 in a translated position.

FIGS. 1-3 illustrate an example of a digitizer pointer 10 according to one implementation. The digitizer pointer 10 may be an all-in-one combination digitizer pointer for so-called "open" spine surgeries. By way of example, the digitizer pointer 10 includes a proximal portion 12, a middle portion 14, and a distal portion 16. By way of example, the proximal portion 12, middle portion 14, and distal portion 16 comprise separate pieces that are assembled to form a single generally cylindrical elongated instrument. The proximal portion 12 includes an elongate tubular member 18 and an inner piston 20. The inner piston 20 includes a threaded post 22 at the proximal end for mating with additional tracking instrumentation, for example an IR-reflective tracking array such as one shown and described in the above-referenced '643 application (incorporated by reference). The elongate tubular member 18 and inner piston 20 comprise the adjustable offset feature component of the digitizer pointer 10. The adjustable offset feature allows the surgeon to add correction in the sagittal plane, and specific elements germane to the adjustable offset feature component are identical in form and function to the corresponding elements shown and described in the above-referenced '643 application (incorporated by reference) and will not be repeated here.

The swivel feature will now be described in more detail. In the example shown and described herein, the swivel feature includes several elements positioned on the distal end 24 of the elongated tubular member 18 working in concert with several elements positioned on the proximal end 26 of the middle portion 14. The distal end 24 of the elongate tubular member 18 comprises a smooth cylindrical post 28. A circumferential recess 30 is formed within the cylindrical post 28, and a raised lip 32 is positioned at the proximal end of the cylindrical post 28. The proximal end 26 of the middle portion 14 comprises a swivel housing 34 including a cylindrical cavity 36 sized and configured to receive the cylindrical post 28 therein. Retention pins 38 extend through pin apertures 40 in the swivel housing 34 and into the cavity 36. Upon assembly, the retention pins 38 occupy space in the circumferential recess 30, and allow for rotational (swivel) movement of the cylindrical post 28 while ensuring the cylindrical post 28 remains within the cavity 36. The raised lip 32 interfaces with the rim of the cavity 36 to form a swivel interface location.

By way of example, the swivel feature may be desirable, according to surgeon preference to re-orient a screw-tulip to align with the other screws (and eventual rod) within a construct. For example, after the digitizer pointer 10 is engaged with a spinal implant (e.g bone screw), the user may manually hold the distal portion of the digitizer pointer 10 (e.g. any suitable place distal of the swivel interface) and swivel the proximal portion of the digitizer pointer 10 (e.g. any suitable place proximal of the swivel interface) about the swivel feature. The proximal portion of the digital pointer 10 is then rotated until the IR array (attached to the threaded post 22) comes in view of the camera.

The translation feature will now be described in more detail. In the example shown and described herein, the translation feature includes several elements positioned on the middle portion 14 working in concert with several elements positioned on the distal portion 16. In addition to the swivel housing 34 previously described, the middle portion 14 includes a elongate shaft 42 extending distally from the swivel housing 34. The elongate shaft 42 includes a proximal segment 44 and a distal segment 46. By way of example, the proximal segment 44 may have a different width dimension (e.g. diameter) than the distal segment 46. In the example shown and described herein, the proximal segment 44 has a width diameter that is greater than the width dimension of the distal segment 46. The proximal segment 44 has a smooth surface to facilitate translation of the distal portion 16, as will be explained below. The proximal segment 44 further has a guide pin 48 extending laterally away from the smooth surface positioned approximately in the middle of the proximal segment 44. The guide pin 48 is received within the shaped track 62 to help control translation of the distal portion 16, as will be explained. The distal segment 46 extends distally from the proximal segment 44 and includes a hex lobe attachment feature 50 positioned at the distal end. The hex lobe attachment feature 50 is configured to engage a spinal implant, for example a bone screw head (not shown). A spring 52 is positioned about the proximal segment 46 and is configured to exert a force on the distal portion 16 to bias the distal portion 16 in an extended position (in which the hex lobe attachment feature 50 is positioned within the fork member 58.

The distal portion 16 comprises an outer sleeve 54 having a track housing 56 at the proximal end, a fork member 58 at the distal end, and an interior lumen 60 extending through the entire length of the distal portion 16. The interior lumen 60 is sized and configured to slideably receive the distal segment 46 of the middle portion 14 therein. The track housing 56 includes a shaped track 62 configured to receive the pin 48 therein. The track 62 may have any shape that facilitates self-locking, for example such the "C"-shape shown by way of example in FIGS. 1-3. The track 62 has a first lock slot 64 positioned at the proximal end of the shaped track 62 and a second lock slot 66 positioned at the distal end of the shaped track 62. The fork member 58 includes a pair of parallel extensions 68 having shaped ends 70 configured to engage a portion of a spinal implant, for example a tulip portion of a rod-receiving bone screw (not shown).

As previously mentioned, the spring 52 exerts a force on the distal portion 16 that biases the distal portion 16 in an extended position. In this position, the pin 48 is positioned within the first lock slot 64 at the proximal end of the shaped track 62. A user may manually engage (e.g. grab) the track housing 56 and rotate the housing 56 such that the guide pin 48 is urged out of the first lock slot 64, along the main portion of the shaped track 62, and into the second lock slot 66. As this happens, the distal portion 16 will be experience translation in a proximal direction. When the pin 48 is fully resting in the second lock slot 66 after translation, the hex lobe attachment feature 50 of the middle portion 14 will extend beyond the fork member 58, as shown in FIG. 3.

The translating feature allows the surgeon to perform two digitizing methods depending on the surgical procedure and the goals of the surgical procedure. In the first setting (in which the pin 48 is in the first lock slot 64), the hex lobe attachment feature 50 is in a retracted position (since the distal portion 16 is extended), and the digitizer pointer 10 can digitize all open, fixed, and connector tulips via engagement between the implanted device and the fork member 58. In the second setting (in which the pin 48 is in the second lock slot 66), the hex lobe attachment feature 50 extends past the distal ends 70 of the fork member 58, and the digitizer pointer 10 can digitize when there has been a lock screw placed. The hex lobe attachment feature 50 mates with a lock screw (not shown) and allows the surgeon to digitize the location of the temporary rod placement. Thus, the surgeon can digitize where the spine is during the temporary rod placement and when final rod bending is being achieved, for example during a pedicle subtraction osteotomy procedure.

While the invention is susceptible to various modifications and alternative forms, specific embodiments thereof have been shown, by way of example only, in the drawings and are herein described in detail. It should be understood, however, that the description herein of specific embodiments is not intended to limit the invention to the particular forms disclosed. On the contrary, the invention is to cover all modifications, equivalents, and alternatives falling within the spirit and scope of the invention as defined herein.

What is claimed is:

1. A device comprising:
a first elongated element comprising a proximal portion of the device, the first elongated element comprising a proximal end and a distal end, the proximal end comprising an attachment element for attaching a tracker to the device, the distal end comprising a recess; and
a second elongated element linearly aligned with the first elongated element and comprising a middle portion of the device, the second elongated element having a proximal elongated shaft segment, a distal elongated shaft segment, and a guide pin extending laterally away from the second elongated element, the proximal elongated shaft segment having a proximal end comprising a cavity formed within the proximal end and a retention element, the retention element configured to engage the recess, the distal elongated shaft segment having a distal end comprising an attachment feature configured to engage a surgical implant, wherein the first elongated element is independently rotatable of the second elongated element.

2. The device of claim 1, wherein the attachment element is a threaded post.

3. The device of claim 1, wherein the distal end of the first elongated element further comprises a smooth post.

4. The device of claim 3, wherein the cavity is configured to receive the smooth post.

5. The device of claim 4, wherein the retention element is configured to prevent the smooth post from ejecting from the cavity.

6. The device of claim 1, wherein the second elongated element is translationally associated with a third elongated element.

7. The device of claim 1, further comprising: a third elongated element linearly aligned with the second elongated element and comprising a distal portion of the device, wherein the third elongated element has a track housing configured to receive the guide pin on the second elongated element, and wherein the second and third elongated elements are slideably associated with one another through movement of the guide pin in the track housing.

8. The device of claim 7, wherein the third elongated element comprises a tubular member including a central lumen extending longitudinally therethrough.

9. The device of claim 8, wherein the second elongated element is slideably received within the central lumen.

10. The device of claim 7, wherein the distal end of the third elongated element comprises a shaped end configured to engage a surgical implant.

11. A device comprising:
a first elongated element comprising a proximal portion of the device, the first elongated element comprising a proximal end, a distal end, a helical slot, a plurality of offset depth slots located around the helical slot, and a helical pin extending laterally away from the first elongated element, the proximal end includes an inner piston comprising an attachment element for attaching a tracker to the device, wherein the inner piston comprises a slot configured to receive the helical pin, wherein the plurality of offset depth slots are configured to receive the helical pin, wherein the proximal end and the inner piston are slideably associated with one another through movement of the helical pin in the helical slot, the distal end comprising a recess; and a second elongated element linearly aligned with the first elongated element and comprising a middle portion of the device, the second elongated element having a proximal elongated shaft segment, a distal elongated shaft segment, and a guide pin extending laterally away from the second elongated element, the proximal elongated shaft segment having a proximal end comprising a cavity formed within the proximal end and a retention element, the retention element configured to engage the recess, the distal elongated shaft segment having a distal end comprising an attachment feature configured to engage a surgical implant, wherein the first elongated element is independently rotatable of the second elongated element.

12. The device of claim 11, further comprising: a third elongated element linearly aligned with the second elongated element and comprising a distal portion of the device, wherein the third elongated element has a track housing configured to receive the guide pin on the second elongated element, and wherein the second and third elongated elements are slideably associated with one another through movement of the guide pin in the track housing.

13. The device of claim 12, wherein the third elongated element further comprises a tubular member including a central lumen extending longitudinally therethrough.

14. The device of claim 11, wherein the second elongated element is slideably received within the central lumen.

15. The device of claim 11, wherein the first elongated element is independently rotatable relative to the second elongated element.

16. The device of claim 11, wherein the first elongated element has a distal end including a smooth post extending distally therefrom.

17. The device of claim 14, wherein the second elongated element has a proximal end including a cavity formed within the proximal end, the cavity configured to receive the smooth post.

18. The device of claim 12, the distal end of the third elongated element comprises a shaped end configured to engage a surgical implant.

19. An apparatus comprising:
a first shaft defining proximal portion of the apparatus and comprising:
a proximal end comprising a first attacher; and
a distal end defining a recess;
a second shaft defining a middle portion of the apparatus and being linearly aligned with the first shaft, wherein the second shaft comprises:
a proximal segment having:
a proximal end defining a cavity formed within the proximal end; and
a retention element engaging the recess;
a distal segment having a distal end comprising a second attacher; and
a guide pin extending laterally away from the second shaft,
a tracker coupled to the first attacher; and
a surgical implant in contact with the second attacher,
wherein the first shaft is independently rotatable of the second shaft.

20. The apparatus of claim 19,
wherein the tracker is an infrared reflective tracking array; and
wherein the surgical implant is a bone screw.

* * * * *